United States Patent [19]

McTiernan et al.

[11] Patent Number: 5,917,123
[45] Date of Patent: Jun. 29, 1999

[54] TRANSGENIC MICE CONTAINING A NUCLEIC ACID ENCODING TUMOR NECROSIS FACTOR-α UNDER THE CONTROL OF A CARDIAC SPECIFIC REGULATORY REGION

[75] Inventors: Charles F. McTiernan, West View; Arthur M. Feldman, Fox Chapel; Toru Kubota; Carole Frye, both of Pittsburgh, all of Pa.

[73] Assignee: University of Pittsburgh, Pittsburgh, Pa.

[21] Appl. No.: 08/818,223

[22] Filed: Mar. 14, 1997

[51] Int. Cl.$^6$ ............................. C12N 5/00; G01N 33/00
[52] U.S. Cl. ........................ 800/18; 800/3; 800/8; 800/9; 800/13; 800/14
[58] Field of Search .................. 800/2, 3, 9, 18, 800/8, 13, 14; 435/6, 331, 320; 530/331, 350; 514/44, 2, 423

[56] References Cited

U.S. PATENT DOCUMENTS 5,266,488  11/1993  Ordahl et al. ..................... 435/240.2

OTHER PUBLICATIONS

Fransen et al. (1985) *Nucleic Acids Research* 13:4417.
Gulick et al. (1991) *J. Biol. Chem.* 266: 9180.
Miyazaki et al. (1995) *J. Clin. Invest.* 96:250.
Pennica et al. (1985) *Proc. Natl. Acad. Sci. USA* 82:6060.
Semon et al. (1987) *Nucleic Acids Research* 15:9083.
Subramaniam et al. (1991) *J. Biol. Chem.* 266:24613.
Miyazaki et al. J. Clin. Invest. vol. 96, 250–259, Jul. 1995.
Hassankhani et al. Devel. Biol. vol. 169, 309–321, May 1995.
Oral et al. Clin. Cardiol vol. 18, 20–27, 1995.
Wagner et al. Genetic Engineering: Principles and Methods vol. 10, pp. 221–246, Plenum Press, 1988.
Houdebine et al. J. biotech. 34, 269–287, 1994.
Wall R.J. Theriogenol. vol. 45, 57–68, 1996.

*Primary Examiner*—Deborah Crouch
*Assistant Examiner*—Michael C Wilson
*Attorney, Agent, or Firm*—Baker & Botts

[57] ABSTRACT

The present invention provides transgenic nonhuman mammals that exhibit elevated levels of tumor necrosis factor alpha in myocardium relative to nontransgenic control mammals, and methods for making transgenic non-human mammals. The invention further provides a method for identifying agents useful in the treatment and prevention of cardiac dysfunction.

10 Claims, 8 Drawing Sheets

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:1:

GGGAAGCTTG ATCTTTGTGA AGGAACC      27

(2) INFORMATION FOR SEQ ID NO:2:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO: 2:

CTTTATGTTT TTGGCGTCTT CCA      23

TRANSGENIC MICE CONTAINING A NUCLEIC ACID ENCODING TUMOR NECROSIS FACTOR-α UNDER THE CONTROL OF A CARDIAC SPECIFIC REGULATORY REGION

BACKGROUND OF THE INVENTION

Tumor necrosis factor alpha (TNFα) is a proinflammatory cytokine with pleiotropic effects (Tracey et al. (1989) *Lancet* 1:1122; Vilĉek et al. (1991) *J. Biol. Chem.* 266:7313). During the past several years, data have accumulated that suggest that TNFα plays a role in the pathophysiology of a variety of cardiac disorders. For example, elevated circulating levels of TNFα have been reported in a variety of cardiac disorders, including acute myocarditis (Matsumori et al. (1994) *Br. Heart J.* 72:561), cardiac allograft rejection (Arbustini et al. (1991) *Am. J. Pathol.* 139:709), myocardial infarction (Latini et al. (1994) *J. Cardiovasc. Pharmacol.* 23:1), and congestive heart failure (Dutka et al. (1993) *Br. Heart J.* 70:141; Torre-Amione et al. (1996) *J. Am. Coll. Cardiol.* 27:1201). Additionally, administration of TNFα causes a left ventricular dysfunction in experimental animals (Murray et al (1996) *Circ. Res.* 78:154) as well as in human subjects (Suffredini et al. (1989) *N. Eng. J. Med.* 321:280; Hegewisch et al. (1990) *Lancet* 335:294). By contrast, neutralization of TNFα with antibodies ameliorates acute myocarditis (Smith et al. (1992) *Circ. Res.* 70:856; Yamada et al. (1994) *Circulation* 89:846) and cardiac allograft rejection (Shrenga et al. (1991) *Transplant Proc* 23:547; Bolling et al. (1992) *Transplantation* 53:283) in experimental animals.

Substantial amounts of TNFα have been detected in the heart after endotoxin administration (Kapadia et al. (1995) *J. Clin. Invest.* 96:1042), during allograft rejection (Arbustini et al. (1991) *Am. J. Pathol.* 139:709), after ischemia (Gurevitch et al. (1996) *J. Am. Coll. Cardiol.* 28:247), and in congestive heart failure (Torre-Amione et al. (1996) *Circulation* 93:704. Inflammatory cells and cardiomyocytes have been suggested as sources of TNFα production (Giroir et al. (1992) *J. Clin. Invest.* 90:693; Habib et al. (1996) *Lancet* 347:1151). However, the physiological significance of this local production of TNFα is not clear.

The foregoing studies suggest a relationship between TNFα production and cardiac dysfunction. However, the nature of this relationship has not heretofore been known. An understanding of the potential role of TNFα in cardiac dysfunction is needed in order to design effective diagnostic and therapeutic agents for cardiac disorders.

The present invention solves this need of the prior art. In accordance with the present invention it has been found that cardiac-specific overexpression of TNFα results in the development of the heart failure phenotype in a transgenic animal model. The present invention thus provides an in vivo model of cardiac dysfunction associated with TNFα overexpression.

SUMMARY OF THE INVENTION

The present invention provides expression vectors comprising a nucleic acid encoding TNFα operably linked to a cardiac-specific regulatory region.

The present invention further provides transgenic non-human mammals whose germ cells and somatic cells contain a nucleic acid encoding TNFα operably linked to a cardiac-specific regulatory region. The transgenic non-human mammals of the present invention are characterized by having significantly higher myocardial levels of TNFα relative to non-transgenic control mammals. In a preferred embodiment the transgenic non-human mammal is a mouse.

In another embodiment, the present invention provides a method of making a transgenic non-human mammal whose germ cells and somatic cells contain a nucleic acid encoding TNFα operably linked to a cardiac-specific regulatory region.

The present invention further provides a method for identifying agents useful in the treatment or prevention of cardiac dysfunction comprising administering the agent to a transgenic non-human mammal of the present invention and assessing the symptoms and progression of cardiac dysfunction in the mammal, wherein an amelioration in symptoms or slowing of progression of cardiac dysfunction relative to untreated transgenic non-human mammals is indicative of an agent useful in the treatment or prevention of cardiac dysfunction.

DETAILED DESCRIPTION OF THE INVENTION

Figure 1:
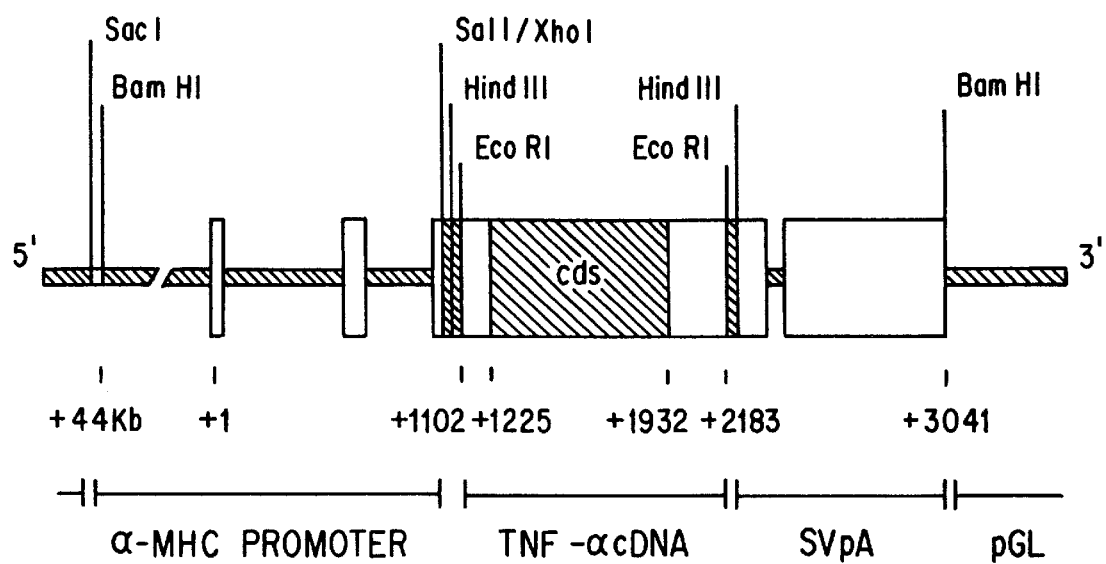
FIG. 1 is a restriction map of pGLMHCTNF1.1. Boxes represent expected exons; cds is the TNFα coding sequence. Positions are numbered relative to the transcription start site of α-MHC.

The present invention provides expression vectors comprising a nucleic acid encoding TNFα operably linked to a cardiac-specific regulatory region. The vectors of the present invention are useful for the expression of TNFα in cardiac cells, for example for the expression of recombinant TNFα in culture, and for the expression of TNFα in cardiac cells in vivo. The vectors are further useful for the production of non-human transgenic mammals whose germ cells and somatic cells contain a gene encoding TNFα operably linked to a cardiac-specific regulatory region.

In the vectors of the present invention, a nucleic acid encoding TNFα is operably linked to a cardiac-specific regulatory region. In accordance with the present invention, "operably linked" means that the regulatory region is capable of directing the cardiac-specific transcription of the nucleic acid encoding TNFα.

Nucleic acids encoding TNFα are known in the art. The nucleotide sequence of murine TNFα is disclosed by Pennica et al. (1985) *Proc. Natl. Acad. Sci. USA* 82:6060 and Semon et al. (1987) *Nucleic Acids Res.* 15:9083, the disclosures of which are incorporated herein by reference, and in GenBank at accession number M11731. The nucleotide sequence of human TNFα is disclosed in U.S. Pat. No. 5,288,852, incorporated herein by reference. Those of ordinary skill in the art can obtain a nucleic acid encoding TNFα by methods known in the art, for example as disclosed by Semon et al. or Fransen et al. (1985) *Nucleic Acids Res.* 13:4417 or by known cloning methods for example as described by Sambrook et al. (1989) *Molecular Cloning: A Laboratory Manual*, 2nd edition, Cold Spring Harbor Laboratory Press, Cold Spring Harbor, N.Y. For example, a nucleic acid encoding murine TNFα can be obtained by treating RAW 264.7 mouse monocyte/macrophage cells (available from the American Type Culture Collection, 12301 Parklawn Drive, Rockville, Md., accession number ATCCTIB71) with lipopolysaccharide for six hours to generate murine TNFα cDNA. The TNFα cDNA may be amplified by standard polymerase chain reaction (PCR) methods using 5' and 3' TNFα cloning primers based upon the known sequence of TNFα. The identity of the nucleic acid as TNFα cDNA can be confirmed by sequence analysis.

In a preferred embodiment of the present invention, the nucleic acid encodes murine TNFα. In another preferred embodiment, the nucleic acid encoding TNFα comprises the coding region, including the coding region for the leader peptide, and the 3' untranslated region (UTR) of the TNFα gene.

In accordance with the present invention, a cardiac-specific regulatory region is defined as a nucleic acid sequence that effects cardiac-specific transcription of the nucleic acid to which it is operably linked. Cardiac specific transcription is transcription that occurs primarily in cardiac tissue, including cardiomyocytes, and may also occur in pulmonary veins and venules (referred to herein as "pulmonary myocardium") with minimal or absent levels of transcription in other cell types. A cardiac-specific regulatory region contains a core promoter element to which an RNA polymerase binds to initiate transcription, and may also contain other regulatory sequences that have an effect on core promoter activity. Cardiac-specific regulatory regions include the α-myosin heavy chain (α-MHC) promoter and the troponin T gene promoter. The troponin T gene promoter is disclosed in U.S. Pat. No. 5,266,488 to Ordahl et al., incorporated herein by reference. In a preferred embodiment, the cardiac-specific regulatory region is the murine α-MHC promoter region. The α-MHC promoter region is contained in a 5.5 kilobase (kb) intergenic region between the mouse α-MHC and β-MHC genes and is described by Subramaniam et al. (1991) *J. Biol. Chem.* 266:24613. As described by Subramaniam et al., the entire intergenic region, or deletions thereof, are capable of directing cardiac-specific expression of a transgene. In particular, a 2.5 kb region containing sequences upstream (5') of the α-MHC transcriptional start site is capable of directing cardiac-specific expression of a transgene and therefore is a cardiac-specific regulatory region as defined in accordance with the present invention. The α-MHC promoter directs expression in myocardial tissue (atria and ventricle) and the pulmonary myocardium of the lung, which is an atrial-like tissue extension into the pulmonary vein. Those of ordinary skill in the art can determine the minimum sequence within the 2.5 kb intergenic region that is sufficient to direct cardiac-specific transcription of a transgene by standard deletion analysis as described by Subramanian et al.

Vectors comprising a nucleic acid encoding TNFα operably linked to a cardiac-specific regulatory region may be made by methods known to those of ordinary skill in the art. Preferred vectors in accordance with the present invention are expression vectors that are compatible with mammalian cells, including plasmid and viral, especially retroviral, vectors. Linearized plasmid vectors are preferred for the production of transgenic mammals by microinjection. Such vectors may be constructed by methods known in the art, or made by modification of commercially available vectors.

In a preferred embodiment of the present invention, the vector is a plasmid vector comprising the α-MHC promoter region operably linked to the coding region and 3' untranslated region (UTR) of the TNFα gene.

The present invention further provides transgenic non-human mammals whose germ cells and somatic cells contain a nucleic acid encoding TNFα operably linked to a cardiac-specific regulatory region. The transgenic non-human mammals of the present invention are characterized by having significantly higher cardiac levels of TNFα relative to non-transgenic control mammals of the same species. In particular, the transgenic animals exhibit statistically significantly ($p<0.001$) higher cardiac levels of TNFα relative to non-transgenic control mammals. In a preferred embodiment the transgenic non-human mammal is a mouse. In another embodiment, the present invention provides a method of making a transgenic non-human mammal whose germ cells and somatic cells contain a nucleic acid encoding TNFα operably linked to a cardiac-specific regulatory region.

The term "transgenic mammals" includes mammals that have foreign DNA segments integrated into their genomes following gene transfer, and mammals in which endogenous genomic DNA has been manipulated, for example by the disruption or deletion of a gene. In the transgenic mammals of the present invention, the foreign DNA segment integrated into the genome is a nucleic acid encoding TNFα operably linked to a cardiac-specific regulatory region. Cardiac-specific regulatory regions and nucleic acids encoding TNFα may not necessarily be foreign to the host mammal. However, a transgene construct containing a nucleic acid encoding TNFα operably linked to a cardiac-specific regulatory region is not endogenous to a host mammal, and therefore the transfer of this transgene construct into a host mammal results in the production of a transgenic mammal.

Methods for making transgenic non-human mammals are known in the art and include, for example, DNA microinjection, embryonic stem (ES) cell transfer, retroviral infection, blastomere-embryo aggregation, teratocarcinoma cell transfer, electrofusion, nuclear transplantation, and spermatozoa-mediated transfer. The methods are reviewed, for example by Pinkert et al., "Transgenic Animal Modeling" in *Molecular Biology and Biotechnology,* Meyers, ed., VCH Publishers, Inc., New York, 1995, pp. 90–907 and numerous laboratory manuals including, for example, Hogan et al. (1994) *Manipulating the Mouse Embryo: A Laboratory Manual,* 2nd edition, Cold Spring Harbor Laboratory Press, Plainview, N.Y., the disclosure of which is incorporated herein by reference. In a preferred embodiment of the present invention, the transgenic nonhuman mammals are produced by microinjection. Transgenic non-human mammals that can be made by the foregoing methods and that are encompassed by the present invention include mice, rats, rabbits, swine, sheep, goats and cattle. In a preferred embodiment of the present invention, the transgenic non-human mammal is a transgenic mouse.

The present invention provides a method of making a transgenic non-human mammal whose germ cells and somatic cells contain a nucleic acid encoding TNFα operably linked to a cardiac-specific regulatory region. The method comprises introducing a nucleic acid encoding TNFα operably linked to a cardiac-specific regulatory region into a zygote of a non-human mammal under conditions whereby the nucleic acid becomes integrated into the genetic material of the zygote, transferring the zygote into the reproductive tract of a pseudopregnant female recipient of a non-human mammal of the same species as the zygote, and maintaining the recipient female under conditions whereby transgenic offspring are produced.

Transgenic mice whose germ cells and somatic cells contain a nucleic acid encoding TNFα operably linked to a cardiac-specific regulatory region and which express TNFα in cardiac tissue may be produced by microinjection as follows. A DNA construct containing a nucleic acid encoding TNFα operably linked to a cardiac-specific regulatory region is microinjected into the pronuclei of fertilized one-cell, zygotes. By transferring the construct into one-cell zygotes, the construct is incorporated into virtually every cell of the transgenic animal. Closed circular or linear DNA may be used, although linear DNA is preferred as it is more readily integrated into the host genome. Linear DNA is produced by restriction endonuclease digestion of the above-described vectors comprising a nucleic acid encoding TNFα operably linked to a cardiac-specific regulatory region. The microinjected zygotes are then surgically transferred to the reproductive tracts of pseudopregnant female mice as described by Hogan et al., and the female recipients carry the embryos to term.

When the mice are about ten or eleven days old, the DNA from the offspring is isolated from tissue samples, for example by tail biopsy, and analyzed to identify individuals that carry the DNA construct containing a nucleic acid encoding TNFα operably linked to a cardiac-specific regulatory region. For example, polymerase chain reaction (PCR) utilizing a 5' primer specific to the α-MHC promoter and a 3' primer specific to the TNFα cDNA can be used to identify the transgenic mice.

In the transgenic mice of the present invention, the nucleic acid encoding TNFα is expressed in cardiac tissue, resulting in elevated levels of TNFα protein in cardiac tissue relative to non-transgenic mice of the same species. Further, the transgenic mice exhibit characteristics of myocarditis and heart failure and thus provide a murine model for cardiac dysfunction. The transgenic mice of the present invention provide an ideal system in which to evaluate the role of TNFα in heart failure by virtue of the fact that failure results from the targeted expression of a single gene (TNFα).

The expression of the nucleic acid encoding TNFα under the control of a cardiac specific regulatory region can be assessed by determining the presence of the corresponding mRNA transcript. The mRNA can be detected by methods known to those of skill in the art, including for example reverse transcriptase polymerase chain reaction (RT-PCR). In RT-PCR, total RNA is first extracted from frozen tissue, for example by an acid guanidinium thiocyanatephenol-chloroform method as described by Chomczynski et al. (1987) *Anal. Biochem.* 162:156, incorporated herein by reference. First-strand cDNA is synthesized using reverse transcriptase and oligo-dT primers, and the cDNA product is then amplified using a 5' primer specific to α-MHC exon 1 and a 3' primer specific to the TNFα cDNA. PCR analysis with primers specific to the endogenous TNFα transcript can be used to compare the expression of the endogenous TNFα gene and the transgenic construct. By RT-PCR, the mRNA transcript corresponding to the nucleic acid encoding TNFα under the control of a cardiac specific regulatory region can be detected in the atrium and ventricle and lung of the transgenic mice, but not in liver. In contrast, the endogenous TNFα gene is expressed in the atrium, ventricle, lung and liver of non-transgenic mice.

The translation of the transcript into TNFα protein can be determined by methods known in the art for the detection of proteins including, for example, immunoblotting, immunoprecipitation, and immunohistochemical staining. For example, tissue levels of TNFα protein can be assessed by an enzyme-linked immunosorbent assay (ELISA) using an antibody for TNFα. An ELISA kit for mouse TNFα (Factor-Test-X) is commercially available from Genzyme Corp., Framingham, Mass. Tissue levels of TNFα can be assessed by ELISA according to the methods disclosed by Pizarro et al. (1993) *Transplantation* 56:399 and Torre-Amione et al. (1996) *Circulation* 93:704, incorporated herein by reference.

The transgenic mice of the present invention have significantly greater amounts of TNFα in myocardium of the atrium and ventricle than age-matched control mice of the same strain. In contrast, the transgenic mice do not have significantly greater amounts of TNFα in the lung or liver relative to control mice. In a preferred embodiment, the transgenic mice have at least about three times, and more preferably at least about five times, higher TNFα protein levels in myocardium of the ventricle and atrium than age-matched control mice as determined by ELISA.

The transgenic mice of the present invention exhibit characteristics of myocarditis and characteristics of heart failure. In particular, the transgenic mice exhibit enlarged hearts and histopathological changes including lymphohistiocytic inflammatory infiltrates. The mice further exhibit re-expression of the atrial natriuretic factor (ANF) gene, a biological change that is characteristic of heart failure. The transgenic mice of the present invention thus provide a model of cardiac dysfunction and are useful for identifying compounds useful for the treatment of cardiac dysfunction.

The present invention further provides a method for identifying agents useful in the treatment or prevention of cardiac dysfunction comprising administering the agent to a transgenic non-human mammal of the present invention and assessing the symptoms and progression of cardiac dysfunction in the mammal, wherein an amelioration in symptoms or slowing of progression of cardiac dysfunction relative to untreated transgenic non-human mammals is indicative of an agent useful in the treatment or prevention of cardiac dysfunction. In a preferred embodiment the transgenic mammal is a transgenic mouse.

The agent to be tested may be administered to the transgenic mammal by methods known to those of ordinary skill in the art and suitable for the selected agent. Possible administration routes include intravascular, intravenous, intra-arterial, subcutaneous, intravascular, intraventricular and oral administration. The agent to be tested may also be administered by gene therapy methods, for example by using adenoviral vectors. Adenoviral vectors may be administered by direct injection into the murine heart in a manner similar to that used for rats and disclosed by Guzman et al. (1993) *Circulation Research* 73:1202, incorporated herein by reference.

The symptoms and progression of cardiac dysfunction may be assessed by histopathology or by determining heart size and function. For example, after administration of the agent to the transgenic mammals for a suitable period of time, the treated mammals are sacrificed and heart masses are determined and compared to non-treated control transgenic mammals.. Myocardial mass can also be determined non-invasively, for example by magnetic resonance imaging. A statistically significant reduction in heart mass relative to non-treated transgenic controls is indicative of an agent useful for the treatment or prevention of cardiac dysfunction.

The following examples further illustrate the present invention.

EXAMPLE I

Materials and Methods
Construction of Vectors

A transgene construct was made containing the murine α-myosin heavy chain (MHC) promoter region and the coding sequence of murine TNFα, followed by the SV40 T antigen intron and polyadenylation signals (SVpA). First, a pGL2-Basic vector (Promega), which has a multiple cloning site, a firefly luciferase gene, and SVpA, was amplified with primers 5'-ggg aag ctt gat ctt tgt gaa gga acc-3' (SEQ ID NO:1, nucleotides 1892–1909, sense strand) and 5'-ctt tat gtt ttt ggc gtc ttc ca-3' (SEQ ID NO:2, complement to nucleotides 77–99) to remove the luciferase gene. After Hind III digestion, the amplified plasmid was self-ligated to generate a pGL-SVpA vector. Finally, a 5.5-kb Sac I-Sal I fragment of the murine α-MHC promoter containing exon 1, exon 2, and 9 bp of exon 3 as described by Gulick et al. (1991) *J. Biol. Chem.* 266:9180, was isolated and ligated into SacI-Xho I digested pGL-SVpA to generate pGL-α-MHC-SVpA.

RAW 264.7 cells treated with lipopolysaccharide for six hours as described by Beutler et al. (1985) *J. Exp. Med.* 161:984 were used to generate complementary DNA (cDNA) to murine TNFα. The cDNA was amplified with a 5' TNF-cloning primer corresponding to TNF cDNA nucleotide numbers 21 through 45, as numbered by Pennica et al. (1985) *Proc. Natl. Acad. Sci. USA* 82:6060 and corresponding to nucleotides 1102 to 1126 of the transgene, wherein 1 is the transcription start site of α-MHC) and the 3'-TNF-cloning primer containing a Bam HI site not found in the murine sequence followed by nucleotides complementary to TNFα cDNA bases 1624–1613 as numbered by Pennica et al. TNFα cDNA was then cloned into the pCR 2.1 vector using a TA Cloning Kit (Invitrogen) to create plasmid TA TNF. The identity of the TNFα coding sequence was confirmed by sequence analysis (Sequenase Version 2.0 DNA Sequence Kit, USB). A 1.1 kb Eco RI-Eco RI fragment of this pCR 2.1-murine TNFα cDNA was ligated with Hind III linkers, and then inserted into the Hind III site of pGL-α-MHC-SVpA to generate pGLMHCTNF1.1. The 1.1 kb fragment corresponds to nucleotides 21 to 1105 as numbered by Pennica et al. and lacks the 3' untranslated region of TNFα that serves as a potent destabilizer.

Figure 2:
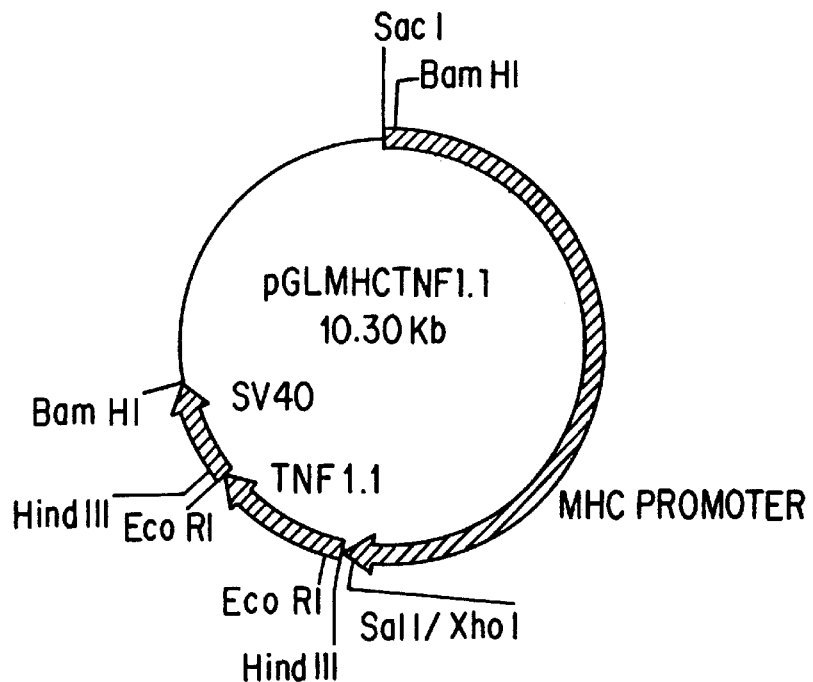
FIG. 2 depicts recombinant plasmid pGLMHCTNF1.1.

The recombinant plasmid pGLMHCTNF1.1 is shown in FIGS. 1 and 2. As depicted therein, the TNFα 3' untranslated region destabilizing sequences were replaced with sequences of the SV40 late gene which do not cause mRNA degradation. FIG. 1 is a restriction map of the transgene. Boxes represent expected exons; cds represents the TNFα coding sequence. Positions are numbered relative to the transcription start site of α-MHC.

Figure 3:
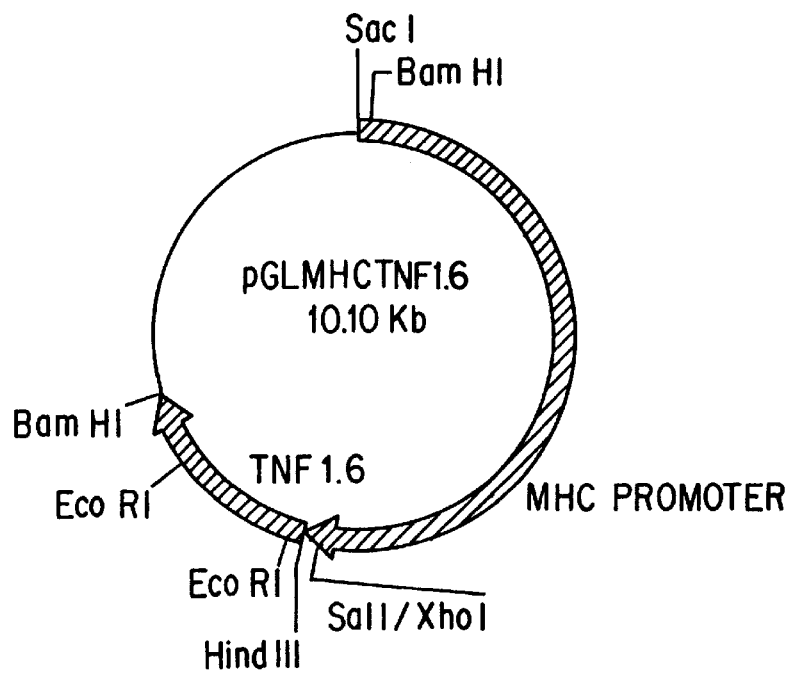
FIG. 3 depicts recombinant plasmid pGLMHCTNF1.6.

A similar method was used to construct a second vector which retains the endogenous TNFα 3' untranslated region and does not contain the SV40 T antigen intron and polyadenylation signals. TA TNF was first digested at the vector EcoRV sites, HindIII linkers added, then digested with HindIII to create a clonable end, and BamHI to cleave at the BamHI site introduced in the initial PCR amplification immediately after TNFα cDNA base 1624. The 1630 bp fragment (containing 7 nucleotides of the HindIII linker, 18 bp of the pCR2.1 vector, TNFα cDNA nucleotides 21–1624 per reference to Penneca et al., and 5 nucleotides from the PCR-introduced BamHI site) was cloned into an 8.4 kbp fragment of pGL-α-MHC-SVpA generated through a HindIII/Partial BamHI digest. This digest removed the SV40 intron and polyadenylation sequence that was present in pGLMHCTNF1.1. The vector is designated pGLMH-CTNF1.6 and is shown in FIG. 3. As depicted therein, this factor contains a 1.6 kb fragment of the TNFα gene containing the coding region and the 3' untranslated region (sequences from 21 through 1624 as numbered by Pennica et al.).

Generation of Transgenic Mice

FVB mice (Taconic Laboratories, Germantown, N.Y.) were used for generation of transgenic mice. The transgene constructs were linearized by Bam HI digestion and microinjected into the pronuclei of one-cell mouse embryos, which were then surgically reimplanted into pseudopregnant female mice as described by Hogan et al. (1994) in *Manipulating the Mouse Embryo: A Laboratory Manual*, 2nd ed., Cold Spring Harbor Laboratory Press, Plainview, N.Y., 217–252. All injections were performed by the Transgenic Core Facility located in the Pittsburgh Children's Hospital. After offspring were born, the tails were biopsied at the age of ten or eleven days. Genomic DNA was isolated using a proteinase K method described by Gross-Bellard et al. (1973) *Eur. J. Biochem.* 36:32. Transgenic mice were identified by polymerase chain reaction (PCR) with a 5' primer specific to the α-MHC promoter (the 5-MHC-exon 2 primer, 5'-cca cat tct tca gga ttc tct-3', SEQ ID NO:3 nucleotides 737 to 757, sense strand, as numbered by Gulick et al., and corresponding to nucleotides 737 to 757 of the transgene) and a 3' primer specific to the TNFα cDNA (the 3' TNF-screening primer, 5'-cag cct tgt ccc ttg aag aga-3', SEQ ID NO:4 nucleotides 579 to 599, antisense strand, as numbered by Fransen et al., and corresponding to nucleotides 1647 to 1667 of the transgene).

Pathological Analysis

Control mice were euthanized under methoxyflurane anesthesia prior to pathological evaluation. All surgical procedures were performed according to the protocols approved by the Institutional Animal Care and Use Committee, University of Pittsburgh. After measurement of body and heart weight, tissues were immersed in cold KCl to arrest the hearts in diastole and immersion fixed in 10% neutral buffered formalin for hematoxylin and eosin (H&E)

staining, or snap-frozen in liquid nitrogen for RNA and protein analysis.

Reverse Transcriptase Polymerase Chain Reaction (RT-PCR)

Total RNA was extracted from frozen tissues by using the acid guanidinium thiocyanate-phenol-chloroform method of Chimczynski et al (1987) *Anal. Biochem.* 162:156. The concentration of RNA in each sample was assessed spectrophotometrically. First-strand cDNA was synthesized by reverse transcription of 1 μg of total RNA by using oligo-dT primers according to manufacturer's instructions (SuperScript II, Gibco BRL). One twentieth of the cDNA product (1 μL) was then amplified with 1.25 U *Thermus aquaticus* DNA polymerase (Gibco BRL) in 50 μL of 20 mmol/L Tris-HCl containing 50 mmol/L KCl, 1.5 mmol/L $MgCl_2$, 200 μmol/L of each DNTP, and 200 mmol/L of specific 5' and 3' primers. PCR reactions were run for 35 cycles of 1 minute of denaturation at 94° C., 30 seconds of annealing at 55° C., and 1 minute of polymerization at 72° C. One fifth of the reaction mixture (10 μL) was subjected to electrophoresis in 2% agarose gel and stained with ethidium bromide.

The PCR reactions utilized the 5' MHC-exon 1 primer (5'-tca gag att tct cca acc cag-3', SEQ ID NO:5, nucleotides 1 to 21, sense strand, as numbered by Gulick et al. and corresponding to nucleotides 1 to 21 of the transgene) and the 3' TNF-screening primer for amplification of the transgene, and the 5' TNF-screening primer (5'-tca gcg agg aca gca agg gac tag-3', SEQ ID NO:6, nucleotides 3 to 28, sense strand, as numbered by Fransen et al.) and 3' TNF-screening primer for amplification of endogenous TNFα. These primers were designed to cross splice-junctions to abrogate amplification of contaminating genomic DNA. Glyceraldehyde-3-phosphate dehydrogenase (GAPDH, Sabath et al. (1990) *Gene* 91:185) was used as an endogenous control to examine the integrity of RNA and the efficiency of reverse transcription.

Enzyme-Linked Immunosorbent Assay (ELISA)

Tissue levels of TNFα protein were assessed using a commercially available ELISA kit for mouse TNFα (Factor-Test-X, Genzyme). Frozen tissues (5 to 20 mg) were suspended in an ice-cold phosphate-buffered saline solution (300 to 500 μL) with protease inhibitors (1 mmol/L phenylmethylsulfonyl fluoride, 0.3 μmol/L aprotinin, 2 μmol/L leupeptin) and homogenized. Tissue homogenates were briefly centrifuged in a microcentrifuge to remove excess particulate matter. Samples were kept on ice for the duration of the assay. Total protein levels were quantitated using a commercially available assay (Bio-Rad Protein Assay, Bio-Rad Laboratories) with bovine serum albumin as a standard (0 to 2 mg/mL). Tissue samples were standardized to 20 μg total protein in 100 μL diluent buffer for each immunoassay. Mouse TNFα provided by the manufacturer was used as a standard (0 to 22409 pg/mL). All assays were done in duplicate. Results were analyzed spectrophotometrically at a wavelength of 450 nm with a microtiter plate reader.

EXAMPLE II

Characterization of TNF1.1 Transgenic Mice

In total, 37 mice were born from 169 eggs injected with the α-MHC-TNF1.1-SVpA (pGLMHCTNF1.1) transgene construct; four of them died spontaneously at 5, 6, 7, and 11 days of age. Since one of the four animals was completely cannibalized, two complete (7-day-old male and 11-day-old female) and one incomplete (5-day-old) carcasses were recovered. PCR analysis revealed all three cadavers as having the transgene. In contrast, none of the surviving mice were transgenic. Transgenic mice having the transgene are designated TNF1.1 mice.

Transgenic mice which died spontaneously at the age of 7 and 11 days were analyzed and compared with age-matched wild-type control mice (n=16 and 17, respectively). Body and heart weights of transgenic mice and age-matched controls are shown below in Table 1.

TABLE 1

|  | Transgenic Mouse | Controls Mean ± SD |
| --- | --- | --- |
| 7-day old |  | n = 16 |
| Body weight, g | 2.9 | 4.2 ± 0.3 |
| Heart weight, mg | 42.2 | 24.9 ± 2.6 |
| 11-day old |  | n = 17 |
| Body weight, g | 4.6 | 6.3 ± 0.5 |
| Heart weight, mg | 84.0 | 32.9 ± 3.8 |

Figure 4A:
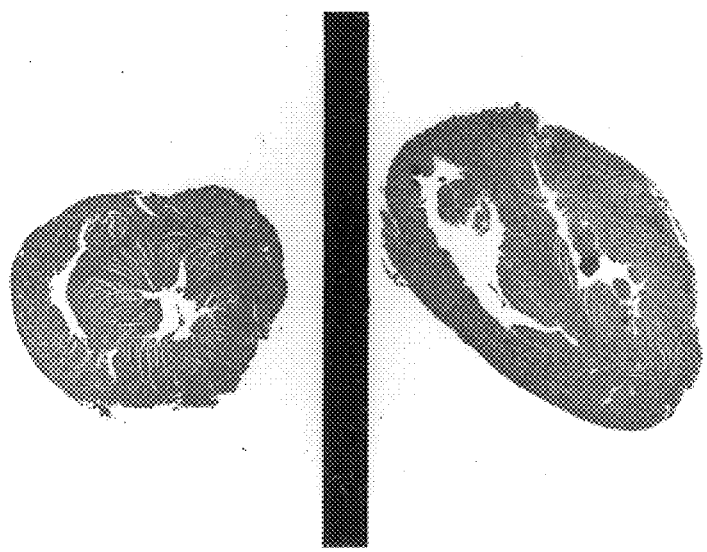
FIG. 4A is a low power photomicrograph (17.5×) of the heart of a control mouse (left panel) in comparison to a transgenic TNF1.1 mouse. Biventricular enlargement and overall increased size of the transgenic heart are evident.

As summarized in Table 1, although the transgenic mice were smaller than the age-matched controls, their hearts were markedly enlarged. FIG. 4A is a low power photomicrograph (H & E; 17.5×) of a control mouse (left) in comparison to a 7-day old transgenic mouse (right). FIG. 4A demonstrates the biventricular enlargement and overall increased size of the heart from the transgenic mouse.

Figure 4B:
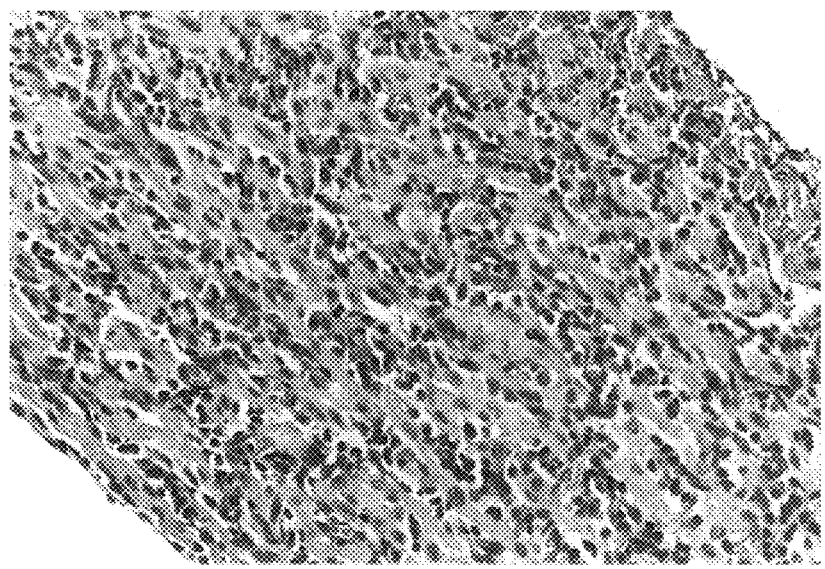
FIG. 4B is a higher magnification (350×) of the transgenic mouse heart of FIG. 4A, demonstrating transmural interstitial inflammation with lymphohistiocytic infiltrate.

FIG. 4B is a higher magnification (H & E; 350×) of the right ventricle from the transgenic mouse heart. As shown in FIG. 4B, routine histopathological examination of the heart of transgenic mice revealed a substantial diffuse mononuclear inflammatory infiltrate, associated with interstitial edema. Despite the myocardial inflammation, coagulative or contraction band myocyte necrosis was not a conspicuous finding. Presence of milk in the stomach of transgenic mice suggested the mode of death as sudden.

Figure 4C:
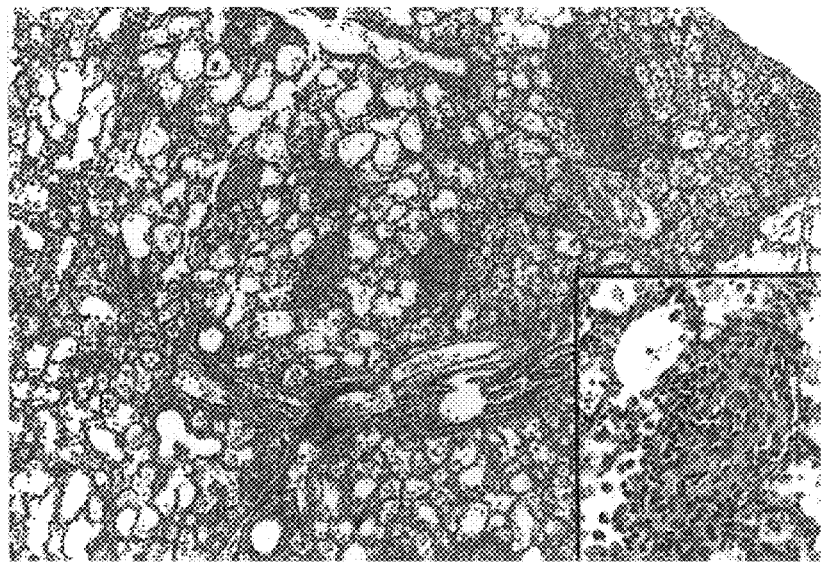
FIG. 4C is a photomicrograph (70×) of the lung of a transgenic TNF1.1 mouse demonstrating perivascular inflammatory infiltrate, similar in quality to that seen in the heart, involving both the pulmonary veins and, in areas, the small pulmonary arteries. The inset at higher magnification (350×) shows the perivascular inflammation that permeates the pulmonary vessel wall and is associated with endothelial cell hypertrophy.

The lung of one transgenic mouse showed a perivascular inflammatory infiltrate, similar in quality to that seen in the heart, involving both the pulmonary veins and in areas, the small pulmonary arteries (FIG. 4C, H&E; 70×). The inset in FIG. 4C at higher magnification (H&E; 350×) shows the perivascular inflammation that permeates the pulmonary vessel wall and is associated with endothelial cell hypertrophy.

The pulmonary vasculature was markedly thickened because of a lymphohistiocytic inflammatory infiltrate that formed a cuff around the adventitia and focally invaded the wall. This was accompanied by edema and separation of mural myocytes. Most of the involved vessels were not contained within the connective sheath surrounding the bronchial tree, and thus most likely represent pulmonary veins, although the same infiltrates were seen around some of the smaller pulmonary arteries. The larger pulmonary arteries coursing with the bronchi were not significantly involved. Although there was a slight increase in intra-alveolar macrophages, no other architectural abnormalities were detected, and the bronchial tree was unremarkable.

The heart and lung of age-matched controls did not show any of the cardiac or pulmonary histopathological changes seen in the transgenic mice. Examination of the liver from one transgenic mouse showed an intact architecture and extramedullary hematopoiesis (appropriate for age), that was diffusely distributed along the sinusoids. The liver of age-matched controls were similar in appearance, although the extramedullary hematopoiesis was distinctly arranged into nodular clusters.

Figure 5:
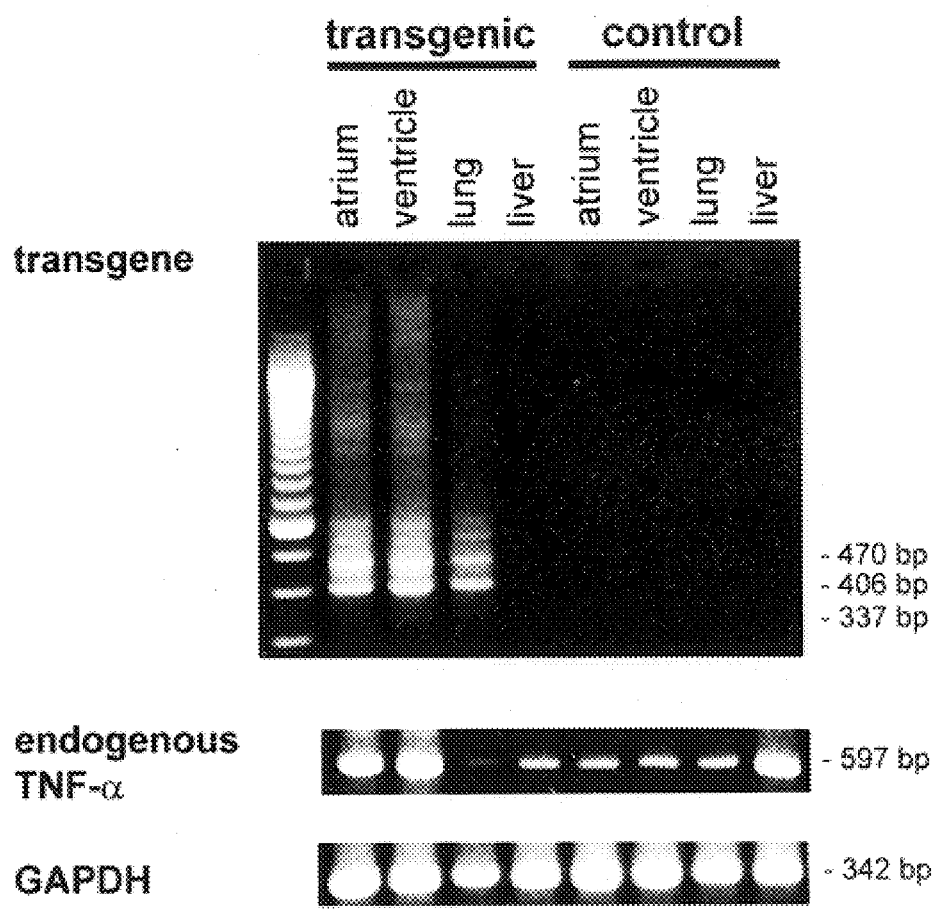
FIG. 5 depicts reverse transcriptase-polymerase chain reaction (RT-PCR) analysis of expression of the transgene and endogenous TNFα in TNF1.1 mice. The ethidium bromide stained gel contains RT-PCR products of RNA isolated from various organs of one transgenic and one control mouse.
Figure 6:
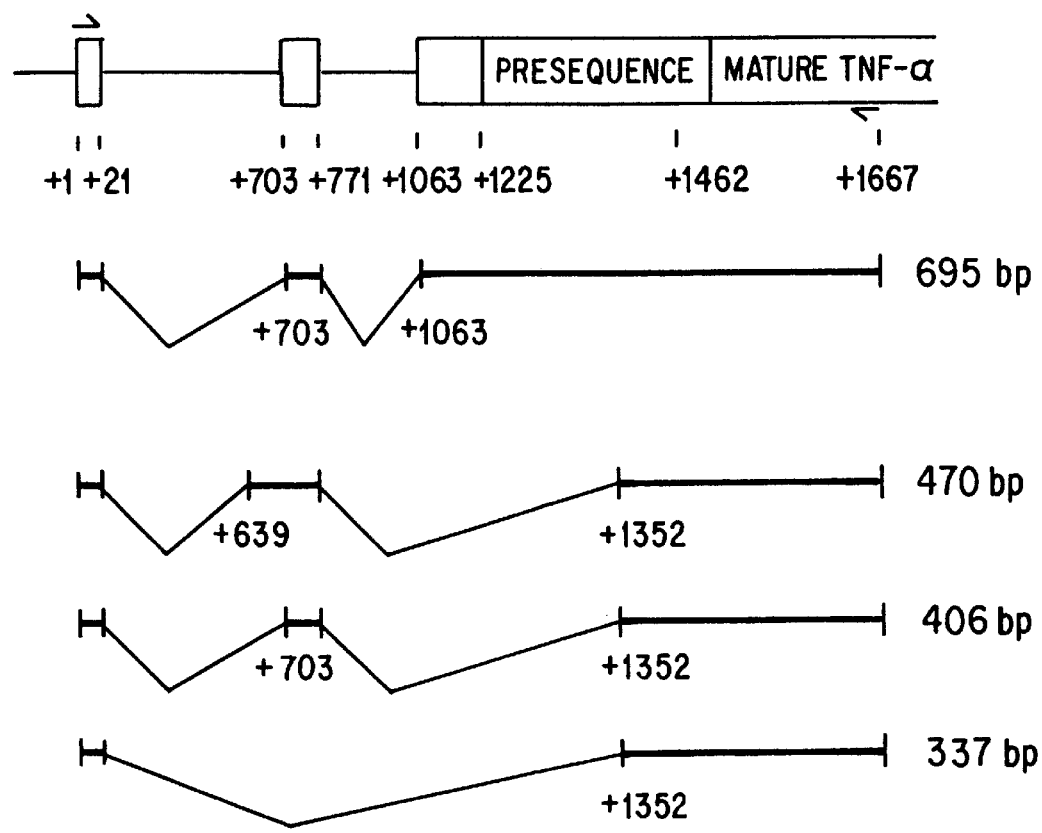
FIG. 6 is a diagram of the TNF1.1 transgene splice products. The top line indicates the expected intron/exon structure of the pGLMHCTNF1.1 transgene construct. Arrows denote the location of PCR primers used to amplify transgene transcripts. Lower lines indicate the maps of the expected (695 bp) and actual (470, 406 and 337 bp) splice products as deduced from dideoxy sequencing of amplified products.

Total RNA was isolated from atrium, ventricle, lung and liver of the transgenic mice. RT-PCR was used to analyze the expression of the transgene and endogenous TNFα in atrium, ventricle, lung and liver. FIG. 5 is a photograph of an ethidium bromide stained gel containing RT-PCR products of RNA isolated from the various organs of one transgenic and one control mouse. The left lane contains a 100 bp size marker ladder (Gibco BRL). RT-PCR demonstrated that the transgene was expressed in the atrium, ventricle and lung of transgenic mice (FIG. 5). Since the size of the PCR products was different from that expected (695 bp), PCR products were cloned to determine the sequence of the transgene transcripts. Sequence analysis revealed that the transgene was spliced as shown in FIG. 6. The top line in FIG. 6 indicates that the expected intron/exon structure of the pGLMHCTNF1.1 transgene construct. The arrows denote the location of PCR primers (5' and 3' TNF-screening primers) used to amplify transgene transcripts. The lower lines indicate map of expected (695 bp) and actual (470, 406, and 337) splice products as deduced from dideoxy sequencing of amplified products.

As shown in FIG. 6, one product (PCR product size 470 bp) contained α-MHC exon 1, 64 bp of intron 1 preceding α-MHC exon 2 and all of exon 2, and was spliced to a near perfect consensus splice-acceptor sequence in the TNFα leader-peptide coding sequence (+1351). The second major splice product (PCR product size 406 bp) consisted of the α-MHC exon 1 and 2 spliced to the same location in the TNFα leader peptide coding region. The third product (PCR product size 337 bp) did not contain the α-MHC exon 2. These splice locations could allow for initiation of translation at the methionine codon (+1444) that occurs in the leader sequence six amino acid residues before leucine 1 (+1462) of the mature, secreted 157 amino acid TNFα protein.

PCR analysis with primers specific to the endogenous TNFα transcript revealed constitutive expression of TNFα in the atrium, ventricle, lung and liver of non-transgenic mice (FIG. 5). Expression of the endogenous TNFα gene appeared elevated in the atrium and ventricle of the transgenic animals, consistent with previous evidence demonstrating that TNFα enhances its own expression in many cell lines.

ELISA was performed to quantitate the amount of TNFα protein in the tissues. The transgenic mouse that died on day 7 and its age-matched controls (n=3) were used. Table 2 presents the tissue TNFα protein levels in the transgenic and control mice as determined by ELISA.

TABLE 2

|  | Transgenic Mouse | Controls Mean ± SD |
| --- | --- | --- |
| TNFα, pg/ml |  | n = 3 |
| Atrium | 2672 | 12 ± 4 |
| Ventricle | 1483 | 23 ± 3 |
| Lung | 25 | 16 ± 4 |
| Liver | 66 | 57 ± 8 |

As shown in Table 2, there were substantial amounts of TNFα protein in the transgenic atrium and ventricle compared to the age-matched controls. In particular, the transgenic mouse had a myocardial TNFα level of 1483 pg/ml compared with a level of 23±3 pg/ml for the wild-type mice.

This example demonstrates that overexpression of TNFα in the heart leads to severe inflammatory cell infiltration and cardiomegaly in a transgenic mouse model. All of the mice harboring the transgene died before the completion of weaning, and all the hearts analyzed had evidence of severe inflammatory cell infiltration. RT-PCR demonstrated expression of the transgene in the heart, and ELISA revealed the presence of substantial amounts of TNFα protein in the transgenic heart. Therefore, it can be concluded that the inflammatory cell infiltration observed in these transgenic mice is not due to an artifact of transgene insertion but arises from expression of the transgene.

EXAMPLE III

Characterization of TNF1.6 Transgenic Mice

Example II demonstrated that the murine α-MHC promoter region can be used to overexpress TNFα specifically in cardiomyocytes of transgenic mice, and that overexpression of TNFα in the heart leads to myocarditis and cardiomegaly. In order to produce transgenic animals that would survive longer, the vector containing the transgene was modified as described in Example I.

The pGLMHCTNF1.1 vector used to produce the transgenic mice in Example I contains the SV40 T-antigen 3' untranslated region in place of the 3' untranslated region of TNFα. As a result it does not have the AU rich sequence found in the 3' untranslated region of the TNFα gene, which is reported to limit steady state levels of TNFα by shortening the half-life of mRNA (Shaw et al. (1986) *Cell* 46:659) and suppressing the translation of the transcripts (Han et al. (1990) *J. Exp. Med.* 171:465). A vector containing the destabilizing region of the 3' untranslated region was constructed as described in Example I and used to produce transgenic mice capable of surviving and producing F1 generations.

Injection of the pGLMHCTNF1.6 construct into fertilized eggs resulted in the production of three founders harboring the TNFα transgene, and the production of a total of 102 transgenic offspring in the F1, F2 and F3 generations. The transgenic TNF1.6 mice exhibit key characteristics of the heart failure phenotype.

Interstitial infiltrates and increased interstitial fibroses were observed in stained myocardium of all transgenic hearts by routine histopathology, and were absent in non-transgenic age-matched littermates.

Figure 7:
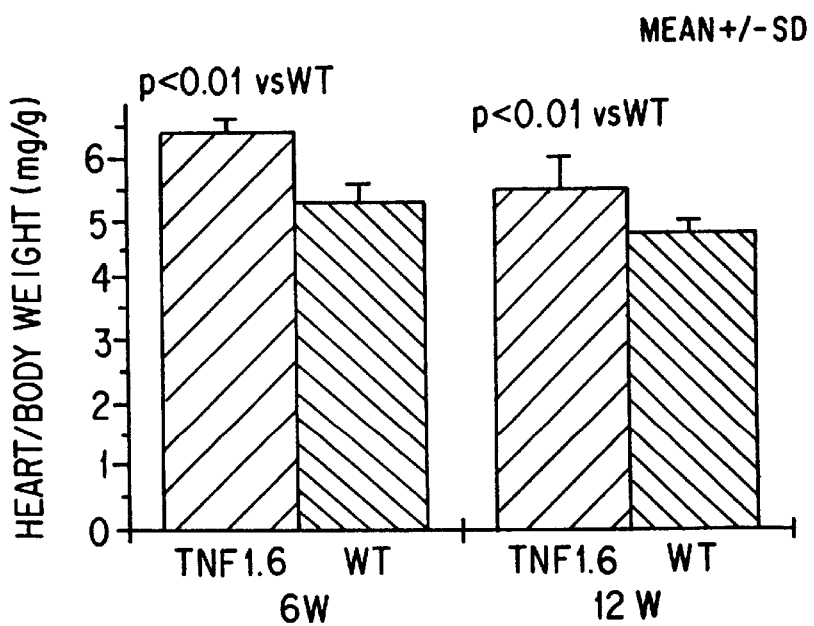
FIG. 7 is a graph of heart weight/body weight ratios for TNF1.6 transgenic mice (TG) and age matched wild type littermates (WT) at 6 and 12 weeks of age.

Heart weight/body weight ratios were determined as described in Example II. FIG. 7 is a graph of heart weight/body weight ratios for TNF1.6 mice (TG) and age-matched wild type littermates (WT) at 6 and 12 weeks of age. As shown in FIG. 7, the TNF1.6 mice exhibited cardiac hypertrophy by heart weight/body weight ratios.

Figure 8:
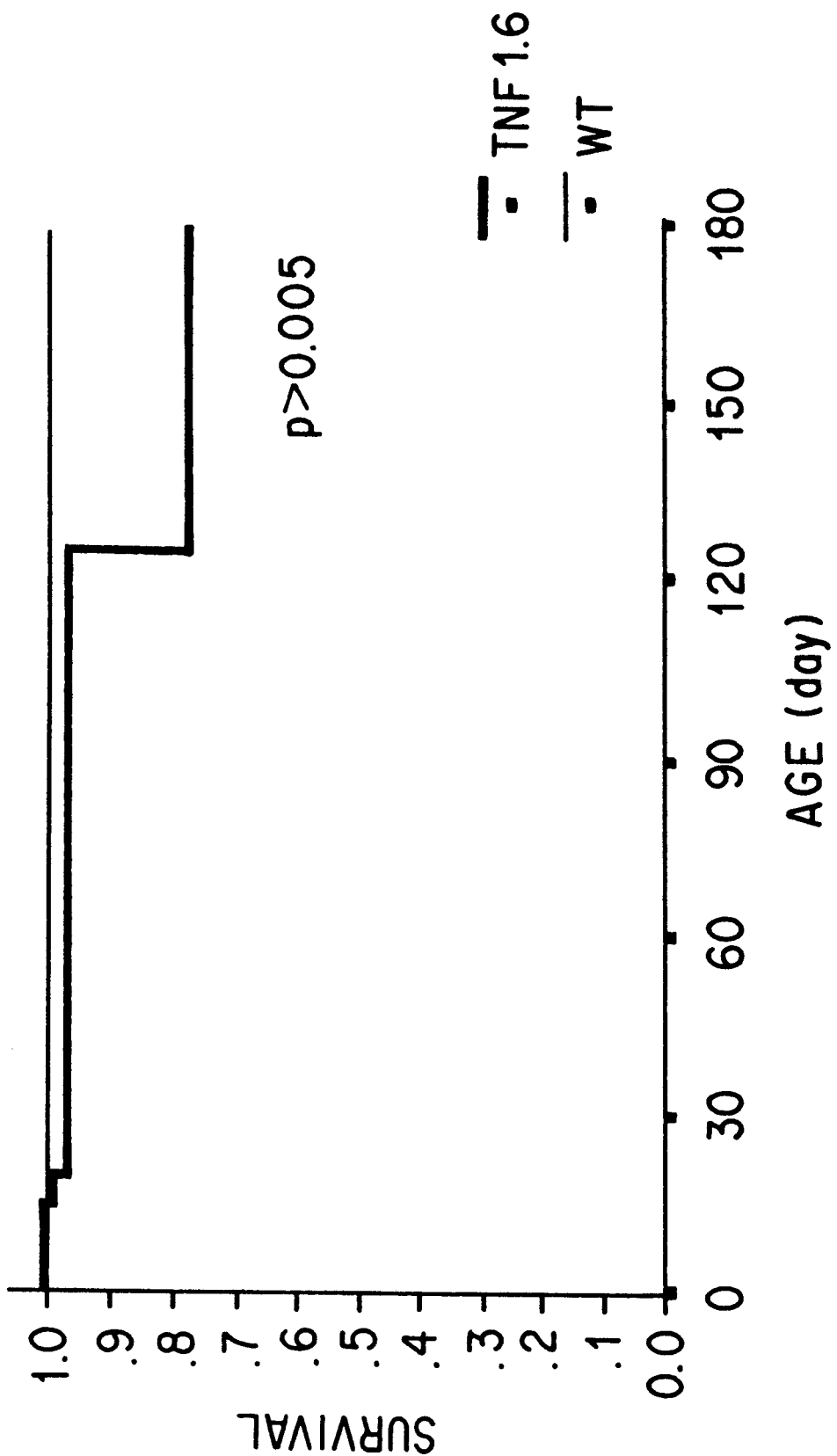
FIG. 8 is a Kaplan-Meyer curve of survival in TNF1.6 mice and age matched littermate controls (P<0.001).

Although no sudden deaths occurred post-natally in wild type mice or in littermates not harboring the transgene, four of the 102 transgenic mice died suddenly. A Kaplan-Meyer curve of survival in TNF1.6 mice and age matched littermates is shown in FIG. 8, and demonstrates significantly ($p<0.001$) increased mortality in transgenic mice as compared to age-matched wild type controls.

Figure 9:
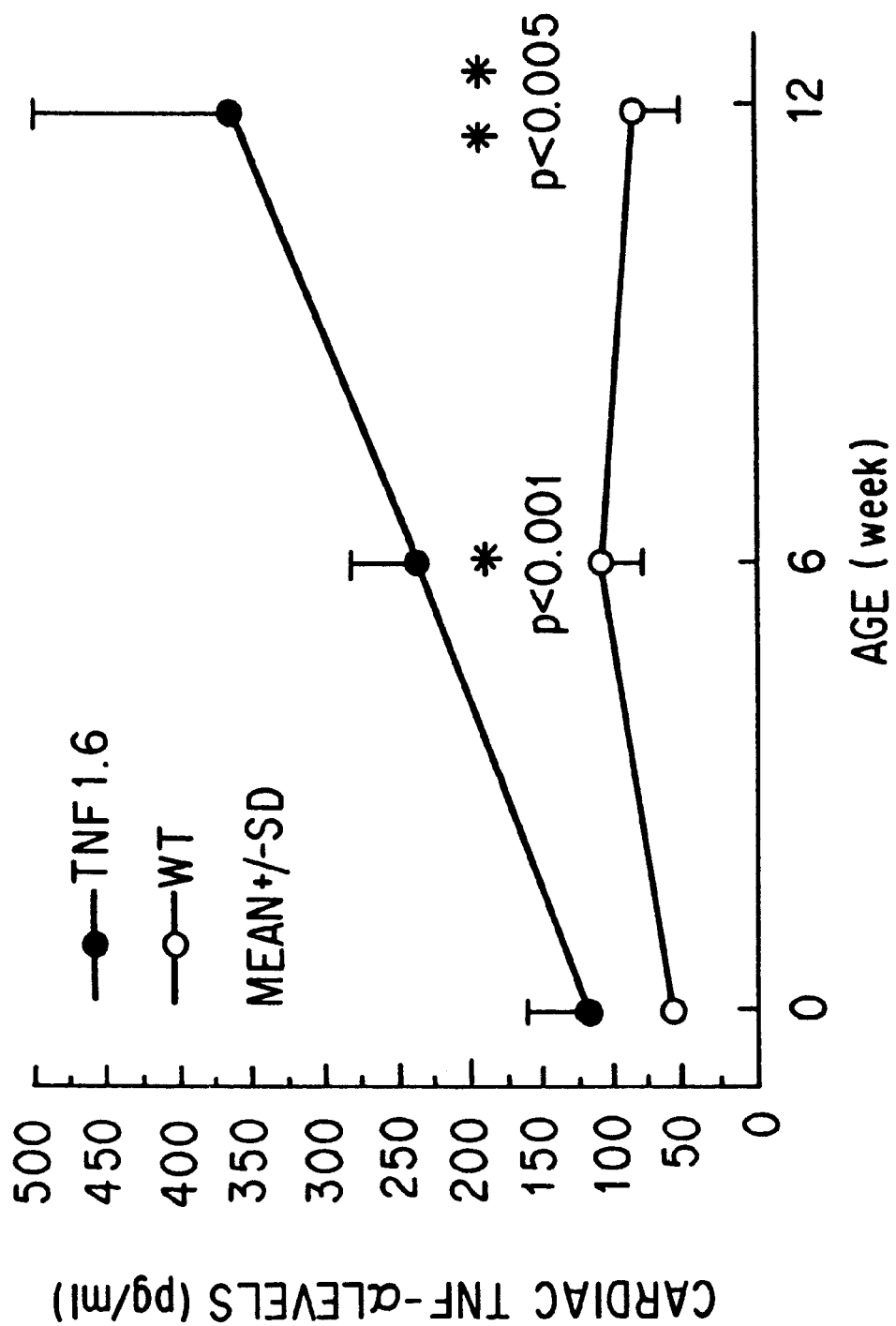
FIG. 9 is a graph of myocardial TNFα levels in TNF1.6 mice and age matched littermate controls.

Myocardial TNFα levels in TNF1.6 mice and age-matched littermate controls were determined by ELISA and are graphed in FIG. 9. As shown in FIG. 9, the TNF1.6 mice have elevations in myocardial TNFα levels that are 7-fold higher than levels found in age matched littermate controls.

Figure 10:
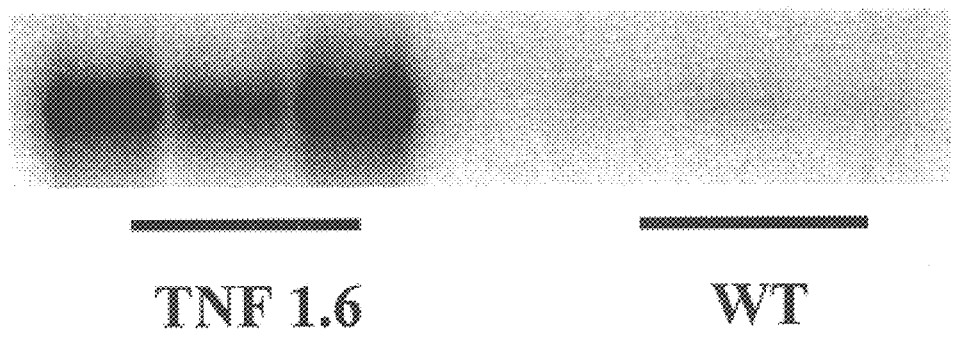
FIG. 10 shows a Northern blot of ANF mRNA from transgenic mice and age-matched wild-type littermates.

Hearts obtained from 12-week-old transgenic mice showed marked expression of atrial natriuretic factor (ANF) mRNA, while ANF mRNA was undetectable in nontransgenic littermate controls. (FIG. 10). The mRNA encoding ANF is not expressed in normal ventricular myodardium. However, re-expression of ANF is associated with cardiac dysfunction and is a classical marker of heart failure.

Accordingly, the marked increase in ANF expression in these transgenic mice provides further evidence that the TNF1.6 transgenic mice replicate human heart failure.

This example demonstrates that TNF1.6 transgenic mice exhibit elevated levels of TNFα in myocardium relative to controls, and exhibit other key characteristics of the heart failure phenotype including cardiac enlargement, interstitial infiltrates and interstitial fibroses.

We claim:

1. A transgenic mouse whose germ cells and somatic cells contain a nucleic acid encoding tumor necrosis factor alpha operably linked to a cardiac-specific regulatory region wherein said mouse expresses said nucleic acid encoding tumor necrosis factor alpha and exhibits myocarditis.

2. The transgenic mouse of claim 1 wherein said nucleic acid encodes murine tumor necrosis factor alpha.

3. The transgenic mouse of claim 1 wherein said nucleic acid encoding tumor necrosis factor alpha comprises the coding and the 3' untranslated region of the murine tumor necrosis factor alpha gene.

4. The transgenic mouse of claim 1 wherein said cardiac-specific regulatory region comprises the murine alpha-myosin heavy chain promoter.

5. A method of making a transgenic mouse whose germ cells and somatic cells contain a nucleic acid encoding tumor necrosis factor alpha operably linked to a cardiac-specific regulatory region wherein said mouse expresses said nucleic acid encoding tumor necrosis factor alpha and exhibits myocarditis, said method comprising introducing a nucleic acid encoding tumor necrosis factor alpha operably linked to a cardiac-specific regulatory region into a zygote of a mouse under conditions whereby said nucleic acid becomes integrated into the genetic material of said zygote, transferring said zygote into the reproductive tract of a pseudopregnant female mouse, and maintaining said female mouse under conditions whereby transgenic offspring are produced.

6. The method of claim 5 wherein said nucleic acid comprises the coding region and the 3' untranslated region of the murine tumor necrosis factor alpha gene.

7. The method of claim 5 wherein said cardiac-specific regulatory region comprises the murine alpha-myosin heavy chain promoter.

8. A method for identifying agents useful for the treatment or prevention of cardiac dysfunction comprising administering an agent to a transgenic mouse whose germ cells and somatic cells contain a nucleic acid encoding tumor necrosis factor operably linked to a cardiac-specific regulatory region and wherein said mouse expresses said nucleic acid encoding tumor necrosis factor alpha and exhibits myocarditis, and assessing the symptoms and progression of cardiac dysfunction in said mouse, wherein an amelioration in symptoms or slowing of progression of cardiac dysfunction relative to untreated transgenic mice is indicative of an agent potentially useful in the treatment or prevention of cardiac dysfunction.

9. The method of claim 8 wherein said nucleic acid comprises the coding region and 3' untranslated region of the murine tumor necrosis alpha gene.

10. The method of claim 8 wherein said cardiac-specific regulatory region comprises the murine alpha-myosin heavy chain promoter.

* * * * *

UNITED STATES PATENT AND TRADEMARK OFFICE
CERTIFICATE OF CORRECTION

PATENT NO. : 5,917,123
DATED : June 29, 1999
INVENTOR(S) : McTiernan, et. al.

It is certified that error appears in the above-identified patent and that said Letters Patent is hereby corrected as shown below:

Column 13, claim 1, line 57: "contain" should read -- comprise -- and "acid encoding" should read --acid construct encoding--;
    line 58: "cardiac-specific regulatory region" should read --myocardial tissue-specific promoter--;
    line 59: "said nucleic acid encoding" should be deleted;
    line 60: "and exhibits myocarditis." should read --, and wher said expression results in the mouse exhibiting at least one symptom of heart failure selected from the group consisting of cardiac enlargement, interstitial infiltrates and interstitial fibrosis.--

Column 13, claim 3, line 65: "encoding tumor necrosis factor alpha" should be deleted;
    line 66: "coding" should read --coding region--.

Column 14, claim 4, lines 1 and 2: "cardiac-specific regulatory region" should rea --myocardial tissue-specific promoter--.

Column 14, claim 5, lines 4-63: delete the text of claim 5 in its entirety and substitute therefor,
--A method of making a transgenic mouse which develops a symptom or symptor of heart failure comprising
    (a) introducing a nucleic acid encoding tumor necrosis factor alpha operably linked to a myocardial tissue-specific promoter into a zygote of a mouse under condition: whereby said nucleic acid construct becomes integrated into the genome of said zygote,
    (b) transferring said zygote into the reproductive tract of a pseudopregnant female mouse,
    (c) maintaining said female mouse under conditions whereby transgenic mice are obtained, wherein said transgenic mice express tumor necrosis factor alpha, and wherein said expression results in at least one symptom of heart failure selected from th( group consisting of cardiac enlargement, interstitial infiltrates and interstitial fibrosis.-- .

UNITED STATES PATENT AND TRADEMARK OFFICE
CERTIFICATE OF CORRECTION

PATENT NO. : 5,917,123
DATED : June 29, 1999
INVENTOR(S) : McTiernan, et. al.

It is certified that error appears in the above-identified patent and that said Letters Patent is hereby corrected as shown below:

Column 15, claim 7, line 1: "cardiac-specific regulatory region" should read
--myocardial tissue-specific promoter--.

Column 15, claim 8, line 4 through col.16, line 4: delete the text of claim 8 in its entirety and substitute therefor,
--A method for identifying agents useful for the treatment or prevention of heart failure comprising
    (a)    administering an agent to a transgenic mouse of claim 1,
    (b)    assessing the symptoms and progression of heart failure in said mouse,
wherein an amelioration in symptoms or slowing of progression of heart failure relative to untreated transgenic mice is indicative of an agent potentially useful in the treatment or prevention of heart failure.--

Column 16, claim 10, line 8: "cardiac-specific regulatory region" should read
--myocardial tissue-specific promoter--.

Signed and Sealed this

Sixth Day of February, 2001

Attest:

Q. TODD DICKINSON

Attesting Officer        Director of Patents and Trademarks